(12) United States Patent
Krapp et al.

(10) Patent No.: US 9,265,250 B2
(45) Date of Patent: Feb. 23, 2016

(54) LIQUID ACTIVE INGREDIENT CONCENTRATES THAT CAN BE EMULSIFIED IN WATER

(75) Inventors: Michael Krapp, Altrip (DE); Klaus Kolb, Schifferstadt (DE); Graham Seaman, Southampton (GB)

(73) Assignee: BASF SE, Ludwigshafen (DE)

( * ) Notice: Subject to any disclaimer, the term of this patent is extended or adjusted under 35 U.S.C. 154(b) by 210 days.

(21) Appl. No.: 13/120,736

(22) PCT Filed: Sep. 25, 2009

(86) PCT No.: PCT/EP2009/062441
§ 371 (c)(1),
(2), (4) Date: Mar. 24, 2011

(87) PCT Pub. No.: WO2010/034808
PCT Pub. Date: Apr. 1, 2010

(65) Prior Publication Data
US 2011/0172101 A1    Jul. 14, 2011

(51) Int. Cl.
*A01N 43/50*    (2006.01)
*A01P 13/00*    (2006.01)
*A01N 33/18*    (2006.01)

(52) U.S. Cl.
CPC ............... *A01N 33/18* (2013.01); *A01N 43/50* (2013.01)

(58) Field of Classification Search
CPC ... A01N 43/50; A01N 33/18; A01N 2300/00; A01N 25/04
USPC ........................................................ 504/139
See application file for complete search history.

(56) References Cited

U.S. PATENT DOCUMENTS

| 4,749,404 | A |   | 6/1988 | Parsons |
|---|---|---|---|---|
| 4,822,405 | A |   | 4/1989 | Martin et al. |
| 5,019,150 | A | * | 5/1991 | Martin et al. ............. 504/130 |
| 5,270,286 | A |   | 12/1993 | Ong |
| 5,405,825 | A | * | 4/1995 | Baker ............................ 504/139 |
| 5,679,619 | A |   | 10/1997 | Morgan et al. |
| 6,323,153 | B1 | * | 11/2001 | Smiley ......................... 504/194 |
| 6,432,884 | B1 | * | 8/2002 | Lachut ......................... 504/363 |
| 6,673,748 | B1 |   | 1/2004 | Foessel |
| 8,877,681 | B2 |   | 11/2014 | Berghaus et al. |

FOREIGN PATENT DOCUMENTS

| EP | 496989 | 8/1992 |
|---|---|---|
| EP | 0933025 | 8/1999 |
| EP | 1042954 | 10/2000 |
| JP | 11-269006 A | 10/1999 |
| KR | 20050003385 | 1/2005 |

OTHER PUBLICATIONS

International Search Report in International Application No. PCT/EP2009/062441, filed Sep. 25, 2009.
International Preliminary Report on Patentability from corresponding International Application No. PCT/EP2009/062441, filed Sep. 25, 2009.

* cited by examiner

*Primary Examiner* — Janet Epps-Smith
*Assistant Examiner* — Courtney Brown
(74) *Attorney, Agent, or Firm* — Brinks Gilson & Lione

(57) ABSTRACT

The present invention relates to a concentrate, comprising:
a) 100 to 400 g/l of a dinitroaniline;
b) 5 to 100 g/l of an imidazolinone ammonium salt or substituted ammonium salt;
c) 20 to 100 g/l of water;
d) 15 to 150 g/l of an anionic surface-active substance which has at least one sulfonic acid group;
e) 5 to 100 g/l of a polymeric, nonionic surface-active substance which has at least one polyethylene oxide group and at least one radical selected from poly-$C_3$-$C_4$-alkylene oxide groups;
f) 50 to 250 g/l of a nonionic surface-active substance selected from ethoxylated fatty acid esters of polyhydroxyl compounds, alkyl polyglucosides, ethoxylated $C_4$-$C_{16}$-alkylphenols and ethoxylated $C_8$-$C_{22}$-alkanols;
g) a hydrocarbon solvent ad 1 l;
where the quantitative data of components a) to f) in g/l are based on the total volume of the active ingredient concentrate.

16 Claims, No Drawings

US 9,265,250 B2

LIQUID ACTIVE INGREDIENT CONCENTRATES THAT CAN BE EMULSIFIED IN WATER

This application is a National Stage application of International Application No. PCT/EP2009/062441 filed Sep. 25,2009, the entire content of which is hereby incorporated herein by reference. This application also claims priority under 35 U.S.C. §119to European Patent Application No. 08165282.8, filed Sep. 26,2008, the entire contents of which is hereby incorporated herein by reference.

DESCRIPTION

The present invention relates to aqueous, water-emulsifiable active ingredient concentrates which comprise at least one herbicidal dinitroaniline, in particular pendimethalin, and at least one imidazolinone herbicide, in particular imazamox.

As is known, the combined use of herbicidal dinitroanilines with imidazolinone herbicides leads to good control of difficult-to-control monocotyledonous and dicotyledonous harmful plants (see e.g. U.S. Pat. Nos. 4,749,404, 4,822,405 and EP 1042954). It is therefore in principle desirable to provide formulations which comprise both active ingredients.

However, the problem arises here that imidazolinone herbicides are often formulated in the form of aqueous concentrates on account of their property of forming water-soluble salts. By contrast, herbicidal dinitroanilines are typically nonpolar compounds with low solubility in water. They are therefore usually formulated in the form of emulsifable concentrates, i.e. in the form of solutions of the dinitroaniline in nonpolar, water-immiscible organic solvents which additionally comprise surface-active substances for emulsifying the solvent. On account of the considerable differences in polarity, it is difficult to provide stable liquid coformulations of both active ingredients.

U.S. Pat. No. 4,822,405 describes a coformulation of imidazolinone herbicides and herbicidal dinitroanilines in the form of an oil-in-water emulsion. In these formulations, the dinitroaniline is present in the form of emulsified droplets of a solution of the dinitroaniline in a water-immiscible organic solvent, whereas the imidazolinone herbicide is present in the form of an ammonium or substituted ammonium salts dissolved in the aqueous phase. Formulations of this type are problematic as regards their storage stability, in particular their storage stability at high and low temperatures. The dilution of the formulation with water required for the application can also lead to problems such as creaming and/or settling of the organic active ingredient phase.

U.S. Pat. No. 4,749,404 in turn describes a coformulation of imazaquin with a dinitroaniline herbicide such as pendimethalin in the form of an emulsifiable concentrate which is obtainable by mixing a solution of imazaquin in an alcohol such as tetrahydrofurfuryl alcohol with a solution of the dinitroaniline in a water-immiscible organic solvent which comprises surface-active substances. The alcohols required to dissolve the imazaquin lead to increased costs of the formulation and are problematic on account of approval restrictions.

U.S. Pat. No. 5,679,619 describes coformulations of pendimethalin with imidazolinone herbicides in the form of suspension concentrates, where pendimethalin is present in the aqueous phase in the form of suspended particles and the imidazolinone herbicide is present in the form of the ammonium salt dissolved in the aqueous phase. These formulations too are unsatisfactory as regards their storage stability. Furthermore, in the case of aqueous suspensions of dinitroanilines, in particular in the case of pendimethalin, there is the danger of a crystallization of the active ingredient, which leads to particle enlargement and thus to settling of the active ingredient.

EP 496989 in turn describes coformulations of imidazolinone herbicides with 2,6-dinitroaniline compounds in the form of emulsifiable concentrates. These formulations comprise relatively large amounts of polar organic solvents such as N-methylpyrrolidone, cyclohexanone or dipropylene glycol which are required to dissolve the imidazolinone herbicide in the water-immiscible phase of the emulsifiable concentrate. These organic solvents are sometimes problematic with regard to their approval and moreover represent an additional cost factor in the production of the formulations.

In the case of the combined application of dinitroanilines and imidazolinone herbicides, it has furthermore proven favorable to apply relatively large amounts of adjuvants, in particular those from the group of ethoxylated fatty acid esters of polyhydroxyl compounds, in order to increase the effectiveness of the aforementioned active ingredients. It is in principle desirable to provide coformulations which already comprise this adjuvant. However, the problem arises here that the incorporation of relatively large amounts of adjuvants in a formulation reduce its storage stability and can lead to problems with the water dilutability.

It is therefore an object of the present invention to provide a storage-stable coformulation of at least one herbicidal dinitroaniline, in particular pendimethalin, with at least one imidazolinone herbicide, in particular imazamox, which comprises a relatively large amount of at least one nonionic surface-active substance which acts as adjuvant, in particular a substance from the group of ethoxylated fatty acid esters of polyhydroxyl compounds. Moreover, the formulation should be characterized by a high dilution stability, i.e. it should be able to be diluted with water without problems and without a separating out of active ingredients and/or other constituents occurring. In particular, it is desirable if polar organic solvents can be dispensed with.

Surprisingly, it has been found that this object is achieved by liquid, water-emulsifiable active ingredient concentrates which comprise the following constituents:

a) 100 to 400 g/l of at least one herbicidal dinitroaniline (constituent a);

b) 5 to 100 g/l of at least one imidazolinone herbicide in the form of its ammonium salt or substituted ammonium salt (constituent b);

c) 20 to 100 g/l of water (constituent c);

d) 15 to 150 g/l of at least one anionic surface-active substance which has at least one sulfonic acid group, in the form of its sodium, potassium, ammonium or substituted ammonium salt (constituent d);

e) 5 to 100 g/l of at least one polymeric, nonionic surface-active substance which has at least one polyethylene oxide group and at least one radical selected from poly-$C_3$-$C_4$-alkylene oxide groups (constituent e);

f) 50 to 250 g/l of at least one nonionic surface-active substance selected from ethoxylated fatty acid esters of polyhydroxyl compounds, alkyl polyglucosides, ethoxylated $C_4$-$C_{16}$-alkylphenols and ethoxylated $C_8$-$C_{22}$-alkanols (constituent f);

g) at least one hydrocarbon solvent ad 1 l (constituent g); where the quantitative data of components a) to f) in g/l are based on the total volume of the active ingredient concentrate.

Accordingly, the present invention firstly provides a liquid, water-emulsifiable active ingredient concentrate comprising the constituents a) to g) in the amounts indicated above. Here, the quantitative data of components a) to f) in g/l are based on the total volume of the active ingredient concentrate.

The invention is associated with a number of advantages: despite the simultaneous presence of water and water-immiscible hydrocarbon solvents in the simultaneous presence of relatively large amounts of different surface-active substances, separation of the formulation does not result. Moreover, the formulation is thermally stable over a relatively long period, i.e. separation phenomena are observed neither upon storage at low temperatures of, for example, below 0° C., for example down to −10° C., nor at high temperatures of above 40° C. or even 50° C. Moreover, the active ingredient concentrates according to the invention are chemically stable, i.e. even upon prolonged storage, usually several months, at elevated temperature, for example at temperatures above 40° C. or even above 50° C., no or at least no noteworthy active ingredient degradation takes place. The active ingredient concentrates according to the invention can be diluted with water without problems even at increased water hardness without resulting in settling or creaming of the active ingredient.

Upon diluting the active ingredient concentrates according to the invention with water, stable emulsions are obtained which generally remain stable for at least 24 h and often at least 48 h without leading to phase separation or even to separating out of the active ingredient. Consequently, the active ingredient concentrates according to the invention and the aqueous dilutions obtainable therefrom permit a trouble free application of the active ingredients.

The viscosity of the active ingredient concentrates according to the invention is low and at 20° C. is typically in the range from 5 to 100, often 10 to 60 and in particular 15 to 35 mPas (determined according to CIPAC MT 22.1).

The active ingredient concentrates according to the invention comprise as constituent a) at least one herbicidal dinitroaniline in an amount of from 100 to 400 g/l, in particular in an amount of from 150 to 300 g/l and particularly preferably in an amount of from 200 to 280 g/l, based on the total volume of the formulation.

Herbicidal dinitroanilines are known to the person skilled in the art, for example from U.S. Pat. Nos. 3,257,190, 3,321,292, 3,367,949 and from C. D. S. Tomlin, "The Pesticide Manual", 13th edition, BCPC (2003) and also from "The Compendium of Pesticide Common Names": HTTP://www.alanwood.net/pesticides/. Examples of dinitroanilines are benfluralin, butralin, dinitramine, ethalfluralin, fluchloralin, isopropalin, methalpropalin, nitralin, oryzalin, pendimethalin, prodiamine, profluralin and trifluralin. Preferred dinitroanilines are pendimethalin and trifluralin. According to a particularly preferred embodiment of the invention, the herbicidal dinitroaniline is pendimethalin.

As further active constituent b), the active ingredient concentrates according to the invention comprise at least one imidazolinone herbicide in the form of its ammonium salt or substituted ammonium salt in an amount of from preferably 7 to 80 g/l, often 8 to 60 g/l and in particular 10 to 50 g/l, based on the total volume of the active ingredient concentrate.

Imidazolinone herbicides typically have a carboxyl group and are therefore able to form a salt with amino bases. Ammonium salts of imidazolinone herbicides are understood as meaning the salt formed by the reaction of the free acid of the imidazolinone herbicide with ammonia. A substituted ammonium salt is understood as meaning the reaction product of the free acid of the imidazolinone herbicide with a primary, secondary or tertiary amine, in particular an amine of the general formula $NR^1R^2R_3$ 

in which $R^1$ is $C_1$-$C_4$-alkyl, which optionally carries a substituent from the group hydroxy or $C_1$-$C_4$-alkoxy, and in which $R^2$ and $R^3$, independently of one another, are hydrogen or have one of the meanings given for $R^1$. Examples of substituted ammonium salts are the ammonium salts of the respective imidazolinone herbicide with methylamine, isopropylamine, dimethylamine, diisopropylamine, trimethylamine, ethylamine, diethylamine, 2-hydroxyethylamine, 2-(2-hydroxyethoxy)eth-1-ylamine, di(2-hydroxy-1-ethyl)amine, benzylamine and the like. Preferred salts are the ammonium salts.

Imidazolinone herbicides and their salts are known to the person skilled in the art, for example from D. L. Schaner, S. L. O'Connor "The Imidazolinone Herbicides", CRC Press Inc., Boca Raton Fla., 1991 and also from "The Compendium of Pesticide Common Names", HTTP://www.alanwood.net/pesticides/. The imidazolinone herbicides include in particular imazamethabenz, imazamox, imazapic, imazapyr, imazaquin and imazethapyr. Preferred imidazolinone herbicides are imazamox, imazapic and imazapyr. In a particularly preferred embodiment of the invention, the imidazolinone herbicide is imazamox. In particular, the active ingredient concentrates according to the invention comprise the aforementioned imidazolinone herbicides in the form of their ammonium salts. In a particularly preferred embodiment, imazamox is in the form of its ammonium salt.

Imidazolinone herbicides have an asymmetry center on the imidazolinone ring and can therefore be present in racemic form or in the form of their R or S enantiomer or in the form of a mixture of the enantiomers, which are enriched with regard to one of the enantiomers. In a preferred embodiment, the active ingredient concentrate comprises the imidazolinone herbicide in the form of the R isomer or in the form of a mixture of the enantiomers which is enriched with regard to the R enantiomer. The enantiomers of the imidazolinone herbicides are known from U.S. Pat. No. 5,973,154 and also from U.S. Pat. No. 6,339,158. In a particularly preferred embodiment, the active ingredient concentrate comprises R-imazamox in the form of an ammonium salt or substituted ammonium salt or a mixture of R-imazamox and S-imazamox in the form of their ammonium salts or substituted ammonium salts which is enriched with regard to R-imazamox.

In the active ingredient concentrates according to the invention, the weight ratio of constituent a) to constituent b) is in the range from 1:1 to 80:1, often in the range from 2:1 to 50:1, preferably in the range from 4:1 to 35:1, in particular in the range from 5:1 to 25:1, or in the range from 5:1 to 30:1, where the imidazolinone herbicide is calculated as free acid.

As further constituent c), the active ingredient concentrates according to the invention comprise 20 to 100 g/l, preferably 40 to 90 g/l and in particular 50 to 80 g/l of water. Preferably, deionized water is used which comprises less than 200 ppm, in particular less than 100 ppm and specifically less than 50 ppm, of polyvalent metal cations such as calcium ions, magnesium ions or iron ions.

As constituent d), the active ingredient concentrates according to the invention comprise at least one anionic surface-active substance which has at least one sulfonic acid group. In the compositions according to the invention, the surface-active substance is present in the form of its sodium, potassium, ammonium or substituted ammonium salt. In this connection, the expressions "ammonium salt" and "substituted ammonium salt" have the meanings specified previously for the ammonium salts and substituted ammonium salts of imidazolinone herbicides. Preferably, the active ingredient concentrate according to the invention comprises the at least one anionic surface-active substance in the form of its ammonium salt.

Constituent d) serves both to stabilize the active ingredient concentrate and also to stabilize the active ingredient emulsion which results upon dilution with water.

Examples of anionic surface-active substances suitable according to the invention are the sodium, ammonium and substituted ammonium salts of:

$C_8$-$C_{22}$-alkylsulfuric acid half-esters (also referred to below as $C_8$-$C_{22}$-alkyl sulfates), such as, for example, lauryl sulfate (dodecyl sulfate), isotridecyl sulfate, cetyl sulfate and stearyl sulfate;

$C_8$-$C_{22}$-alkylsulfonic acids (also referred to below as $C_8$-$C_{22}$-alkylsulfonates), such as, for example, laurylsulfonate, isotridecylsulfonate, cetylsulfonate and stearylsulfonate;

arylsulfonic acids, in particular $C_1$-$C_{16}$-alkylbenzenesulfonic acids, such as, for example, cumylsulfonic acid, octylbenzenesulfonic acid, isooctylbenzenesulfonic acid, nonylbenzenesulfonic acid, decylbenzenesulfonic acid, dodecylbenzenesulfonic acid, isotridecylbenzenesulfonic acid, tetrapropylenebenzenesulfonic acid, $C_{10}$-$C_{13}$-alkylbenzenesulfonic acid, naphthylsulfonic acid, mono- and di-($C_1$-$C_{16}$)-alkylnaphthylsulfonic acid, such as, for example, dibutylnaphthylsulfonic acid;

mono- and di-(C1-C16)-alkyl diphenyl ether (di)sulfonic acids, such as, for example, dodecyl diphenyl ether disulfonate;

sulfates and sulfonates of fatty acids and fatty acid esters;

oligooxy-($C_2$-$C_3$)-alkylene-($C_8$-$C_{22}$)-alkyl ether sulfates, in particular of sulfuric acid half-esters of the ethoxylated ($C_8$-$C_{22}$)-alkanols, such as, for example, sulfuric acid half-esters of ethoxylated lauryl alcohol, ethoxylated cetyl alcohol or ethoxylated stearyl alcohol;

oligooxy-($C_2$-$C_3$)-alkylene-($C_1$-$C_{16}$)-alkylbenzene ether sulfates, in particular sulfates of the ethoxylates of ($C_1$-$C_{16}$)-alkylphenols;

mono- and di-($C_4$-$C_{18}$)-alkyl esters of sulfosuccinic acid (=($C_4$-$C_{18}$)-dialkyl sulfosuccinates), such as, for example, dioctyl sulfosuccinate;

condensates of naphthalinesulfonic acid, of ($C_1$-$C_{16}$)-alkylnaphthalinesulfonic acid or phenolsulfonic acid with formaldehyde (=($C_1$-$C_{16}$)-naphthalinesulfonate-formaldehyde condensates, ($C_1$-$C_{16}$)-alkylnaphthalinesulfonate-formaldehyde condensates and phenolsulfonate-formaldehyde condensates);

oligooxy-($C_2$-$C_3$)-alkylenemono-, -di- and -tristyrylphenyl ether sulfates, in particular oligoethoxylates of mono-, di- and tristyrylphenol;

Among these, preference is given to:

the sodium and ammonium salts of $C_4$-$C_{20}$-alkylbenzenesulfonic acids, for example the sodium and ammonium salts of octylbenzenesulfonic acid, isooctylbenzenesulfonic acid, nonylbenzenesulfonic acid, decylbenzenesulfonic acid, dodecylbenzenesulfonic acid, isotridecylbenzenesulfonic acid, tetrapropylenebenzenesulfonic acid, $C_{10}$-$C_{13}$-alkylbenzenesulfonic acid and mixtures, in particular isomer mixtures of the aforementioned alkylbenzenesulfonic acids, where the ammonium salts of the aforementioned alkylbenzenesulfonic acids are particularly preferred;

the sodium and ammonium salts of $C_8$-$C_{22}$-alkylsulfuric acid half-esters (also referred to below as sodium or ammonium salts of $C_8$-$C_{22}$-alkyl sulfates), in particular the sodium and ammonium salts of lauryl sulfate, dodecyl sulfate, isotridecyl sulfate, cetyl sulfate and stearyl sulfate;

sodium and ammonium salts of mono- and di-$C_4$-$C_{18}$-alkyl esters of sulfosuccinic acid, in particular the sodium and ammonium salts of the dihexyl ester of sulfosuccinic acid, of the di-n-octyl ester of sulfosuccinic acid, of the diiso-octyl esters of sulfosuccinic acid and of the di-2-ethylhexyl ester of sulfosuccinic acid; and mixtures of the aforementioned anionic surface-active substances.

Among these, particular preference is given to the sodium and ammonium salts of $C_4$-$C_{20}$-alkylbenzenesulfonic acids, for example the sodium and ammonium salts of octylbenzenesulfonic acid, isooctylbenzenesulfonic acid, nonylbenzenesulfonic acid, decylbenzenesulfonic acid, dodecylbenzenesulfonic acid, isotridecylbenzenesulfonic acid, tetrapropylenebenzenesulfonic acid, $C_{10}$-$C_{13}$-alkylbenzenesulfonic acid, and mixtures, in particular isomer mixtures of the aforementioned alkylbenzenesulfonic acids, where the ammonium salts of the aforementioned alkylbenzenesulfonic acids are very particularly preferred.

In one particularly preferred embodiment of the invention, the active ingredient concentrate comprises, as component d), at least one ammonium salt of a $C_4$-$C_{20}$-alkylbenzenesulfonic acid and in particular the ammonium salt of a $C_8$-$C_{16}$-alkylbenzenesulfonic acid, e.g. the ammonium salt of octylbenzenesulfonic acid, of isooctylbenzenesulfonic acid, of nonylbenzenesulfonic acid, of decylbenzenesulfonic acid, of dodecylbenzenesulfonic acid, of isotridecylbenzenesulfonic acid or a mixture of these ammonium salts.

The active ingredient concentrate according to the invention often comprises constituent d) in an amount of from 20 to 100 g/l, preferably 20 to 80 g/l, in particular in an amount of from 20 to 50 g/l, based on the total volume of the active ingredient concentrate.

Furthermore, as constituent e), the active ingredient concentrate according to the invention comprises a nonionic surface-active substance which has at least one, e.g. one or two polyethylene oxide groups and at least one, e.g. one or two poly-$C_3$-$C_4$-alkylene oxide groups, in particular at least one, e.g. one or two polypropylene oxide groups. In addition, the nonionic surface-active substance can also have one or more, e.g. one, $C_1$-$C_{10}$-alkyl radical. Preferably, the polymeric, nonionic surface-active substance has a number-average molecular weight of at least 1500 Daltons, e.g. 1500 to 100000 Daltons, in particular at least 2000 Daltons, e.g. 2000 to 40000 Daltons. Preferably, the nonionic surface-active substance has a HLB value according to Griffin in the range from 5 to 20 and in particular in the range from 8 to 18.

Preferably, the polymeric nonionic surface-active substance is selected from ethylene oxide propylene oxide block copolymers, in particular from ethylene oxide-propylene oxide diblock copolymers and ethylene oxide-propylene oxide triblock copolymers, where the di- and triblock copolymers can also have a $C_1$-$C_{10}$-alkyl radical. The number-average molecular weight of the ethylene oxide-propylene oxide diblock copolymers and triblock copolymers is preferably in the range from 1500 to 100000 Daltons, in particular 2000 to 40000 Daltons.

The active ingredient concentrate according to the invention often comprises constituent e) in an amount from 7 to 80 g/l, preferably 10 to 70 g/l, in particular in an amount of 15 to 50 g/l, based on the total volume of the active ingredient concentrate.

Preferably, the weight ratio of constituent d) to constituent e) in the active ingredient concentrates according to the invention is in the range from 20:1 to 1:5, often 10:1 to 1:3, and in particular in the range from 5:1 to 1:2.

As further constituent f), the active ingredient concentrate according to the invention comprises at least one nonionic, surface-active substance, which is also referred to as adjuvant. According to the invention, this is selected from ethoxylated fatty acid esters of polyhydroxyl compounds, alkyl polyglucosides, ethoxylated $C_4$-$C_{16}$-alkylphenols and ethoxylated $C_8$-$C_{22}$-alkanols and mixtures of these substances. The amount of constituent f) is often 100 to 250 g/l and preferably 150 to 200 g/l, based on the total volume of the active ingredient concentrate according to the invention.

The ethoxylated fatty acid esters of polyhydroxyl compounds are generally ethoxylates of mono-, di- or triesters of fatty acids with aliphatic or cycloaliphatic polyhydroxyl compounds which generally have 3, 4, 5 or 6 hydroxyl groups and 3, 4, 5 or 6 carbon atoms, where the nonethoxylated esters of the fatty acids with polyhydroxyl compounds generally also have at least one, preferably 2, 3 or 4 free hydroxyl groups. The fatty acid constituents in these substances are usually derived from saturated, mono- or polyunsaturated fatty acids, where the fatty acids generally have 6 to 22 and in particular 8 to 18 carbon atoms. Examples of suitable fatty acid constituents in these substances are saturated fatty acids such as lauric acid, myristic acid, palmitic acid, margaric acid, stearic acid, arachic acid, behenic acid, lignoceric acid and cerotic acid, unsaturated fatty acids such as undecylenic acid, palmitoleic acid, oleic acid, elaidic acid, vaccenic acid, icosenic acid, cetoleic acid, erucic acid and nervonic acid derived radicals, and also polyunsaturated fatty acids such as linoleic acid, α-linolenic acid, γ-linolenic acid, arachidonic acid, timnodonic acid, clupanodonic acid and cervonic acid, and also mixtures of the aforementioned fatty acids.

Among these, preference is given to ethoxylated monofatty acid esters of glycerol and ethoxylated mono- and difatty acid esters of sorbitan and of sorbitan anhydride, where the fatty acid radicals in these compounds have preferably 8 to 20 and in particular 10 to 18, carbon atoms. The fatty acid radicals may be saturated or mono- or polyunsaturated and are typically derived from the aforementioned fatty acids and their mixtures, in particular from lauric acid, myristic acid, palmitic acid, margaric acid, stearic acid, palmitoleic acid, oleic acid, linoleic acid and mixtures thereof.

The degree of ethoxylation, i.e. the average number of repeat units derived from ethylene oxide, is typically 5 to 50 and in particular 10 to 40 (number average).

Alkyl polyglucosides are understood as meaning nonionic surfactants which are obtainable by the acid-catalyzed reaction of glucose or starch with fatty alcohols which generally have 8 to 22 carbon atoms (see also Römpp-Lexikon Chemie, Vol. 1. A-Cl, page 118, $10^{th}$ completely revised edition, 1996, Thieme Verlag, Stuttgart, New York). Alkyl polyglucosides typically have the following structure:

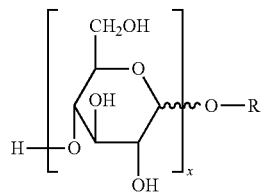

in which x is on average 1.1 to 2.0 and in particular 1.2 to 1.6, and R is a linear or branched alkyl radical having preferably 8 to 22 carbon atoms bonded via the anomeric oxygen atom of the glucose.

Among the ethoxylated $C_4$-$C_{16}$-alkylphenols, preference is given to those with a degree of ethoxylation in the range from 2 to 40 and in particular in the range from 4 to 30, for example ethoxylated octylphenol, ethoxylated nonylphenol, ethoxylated dodecylphenol and ethoxylated isotridecylphenol.

Among the ethoxylated $C_8$-$C_{22}$-alkanols, preference is given to those with a degree of ethoxylation of from 2 to 40 and in particular 4 to 30, in particular ethoxylated $C_{10}$-$C_{18}$-alkanols, such as ethoxylated decanol, ethoxylated dodecanol, ethoxylated tridecanol, ethoxylated isotridecanol, ethoxylated lauryl alcohol and ethoxylated stearyl alcohol.

As component f), in particular ethoxylated fatty acid ester of sorbitan, in particular ethoxylated monofatty acid esters of sorbitan (polysorbates) are preferred, where the fatty acid radical typically has 8 to 22 carbon atoms and in particular 10 to 18 carbon atoms and is in particular derived from one of the following fatty acids or a mixture thereof: lauric acid, myristic acid, palmitic acid, margaric acid, stearic acid, palmitoleic acid, oleic acid and linoleic acid. The degree of ethoxylation here is typically in the range from 5 to 40 and particularly preferably in the range from 10 to 30. In a very particularly preferred embodiment of the invention, component f) is ethoxylated sorbitan monolaurate.

As further component, the compositions according to the invention comprise at least one hydrocarbon solvent. The amount of hydrocarbon solvents will typically be in the range from 100 to 750 g/l and in particular in the range from 200 to 600 g/l, based on the total volume of the formulation. Preferably, the hydrocarbon solvent has a boiling point at atmospheric pressure in the range from 120 to 300° C., in particular in the range from 150 to 250° C. Within the context of this invention, aromatic hydrocarbons are understood as meaning mono- and polynuclear aromatics which optionally carry one or more aliphatic substituents, in particular alkyl groups. These include, besides toluene, xylenes, in particular mixtures of aromatic hydrocarbons which are obtained as fractions during the distillation, in particular from petroleum products, in the stated boiling point range. These include, in particular, commercial products which are known under the trade names Solvesso®, in particular Solvesso® 100, Solvesso® 150, Solvesso® 200, Solvesso® 150 ND, Solvesso® 200 ND, Aromatic®, in particular Aromatic® 150 and Aromatic® 200, Hydrosol®, in particular Hydrosol® A 200 and Hydrosol® A 230/270, Caromax®, in particular Caromax® 20 and Caromax® 28, Aromat K 150, Aromat K 200, Shellsol®, in particular Shellsol® A 100 and Shellsol® A 150, and Fin FAS-TX, in particular Fin FAS-TS 150 and Fin FAS-TX 200. Particular preference is given to the mixtures Solvesso® 150 ND and Solvesso® 200 ND (ExxonMobil Chemical), in which the potential carcinogen naphthaline has been depleted. Thus, Solvesso® 150 ND comprises predominantly aromatic hydrocarbons having 10 or 11 carbons which boil in the range from 175 to 209° C. and which are predominantly alkylbenzenes, whereas Solvesso® 200 ND comprises predominantly aromatic hydrocarbons having 10 to 14 carbon atoms which boil in the range from 235 to 305° C. and which are predominantly alkylnaphthalines. A further example of the aromatic hydrocarbons named here is a product marketed under the trade name Hisol SAS-296, which is a mixture of 1-phenyl-1-xylylethane and 1-phenyl-1-ethylphenylethane.

The aforementioned constituents a) to g) generally constitute at least 95% by weight, in particular at least 99% by weight and specifically at least 99.5% by weight, of the active ingredient concentrate according to the invention.

It has proven advantageous if the active ingredient concentrate according to the invention comprises, based on its total weight, not more than 5% by weight, in particular not more than 1% by weight and specifically not more than 0.5% by weight or essentially no water-miscible organic solvents. These are to be understood as meaning organic substances which are liquid at room temperature and which, at 25° C., have a solubility in water of at least 50 g/l, often at least 100 g/l. These include $C_1$-$C_4$-alkanols such as methanol, ethanol, propanol, isopropanol and n-butanol, $C_2$-$C_6$-alkylene glycols such as ethylene glycol, propylene glycol, butylene glycol, hexylene glycol, di- and trialkylene glycols, N-alkyl lactams such as N-methylpyrrolidone, N-ethylpyrrolidone, dialkyl-sulfones such as dimethyl sulfoxide, cyclic ethers such as tetrahydrofuran, dioxane and tetrahydrofurfuryl alcohol.

Furthermore, for the stability of the formulation, it has proven advantageous if it comprises less than 200 ppm, in particular less than 100 ppm and particularly preferably less than 50 ppm polyvalent metal cations, for example alkaline earth metal cations, iron ions and other transition metal cations.

Besides the aforementioned constituents, the active ingredient concentrates according to the invention can comprise further constituents, as are customarily used in formulations. These include agents for adjusting the pH, in particular acids, for example alkanecarboxylic acids having 1 to 10 carbon atoms, such as acetic acid and propionic acid and the salts thereof, in particular the ammonium, sodium and potassium salts thereof, such as ammonium acetate, sodium acetate, potassium acetate and sodium propionate, ammonia, amine bases, e.g. the aforementioned amines of the formula $NR^1R^2R^3$, (in)organic buffer salts such as hydrogencarbonates, carbonates, hydrogenphosphates, dihydrogenphosphates such as sodium hydrogencarbonate, potassium hydrogencarbonate, disodium hydrogenorthophosphate, sodium dihydrogenorthophosphate, sodium ammoniumorthophosphate, potassium hydrogenphosphate, dipotassium hydrogenorthophosphate, potassium dihydrogenorthophosphate, potassium ammonium hydrogenorthophosphate and the like. The amount of such agents will generally not exceed 0.5 g/l and is often in the range from 0.1 to 5 g/l, based on the total volume of the formulation. Preferably, the amount of these agents is chosen such that the resulting pH of the aqueous phase is in the range from 5 to 9 and in particular in the range from 6 to 8.

Furthermore, the active ingredient concentrates according to the invention can comprise antifoams. Suitable antifoams comprise polysiloxanes, such as, for example, polydimethylsiloxane, long-chain alcohols, organofluorine compounds, fatty acids and salts thereof, and also mixtures thereof. Antifoams are usually used in amounts of from 0.01 to 1 gram per liter of the active ingredient concentrate.

Furthermore, the active ingredient concentrates according to the invention can comprise preservatives. Suitable preservatives for avoiding bacterial infestation of the compositions according to the invention comprise formaldehyde, alkyl esters of para-hydroxybenzoic acid, sodium benzoate, 2-bromo-2-nitropropane-1,3-diol, ortho-phenylphenol, dichlorophene, benzyl alcohol hemiformal, thiazolinone and isothiazolinone derivatives, such as, for example, alkyl-isothiazolinones and benzisothiazolinones, 5-chloro-2-methyl-4-isothiazolinone, pentachlorophenol, 2,4-dichlorobenzyl alcohol and mixtures thereof. Examples of suitable commercially available bactericidal products are Proxel® (ICI), Acticide® RS (Thor Chemie), Kathon® (Rohm & Haas) and Acticide MBS (Thor Chemie). As a rule, the fraction of preservatives will not exceed 1 g/l and will usually be in the range from 0.01 to 1 gram per liter.

The active ingredient concentrates according to the invention can generally be prepared easily by mixing the ingredients until a liquid which appears homogeneous has formed. In what order the addition of the ingredients takes place is usually of secondary importance. For example, the constituents can be added to one container and the mixture obtained in this way is homogenized, for example by stirring, until a homogeneous liquid has formed. Preferably, the dinitroaniline will firstly be dissolved in some or all of the hydrocarbon solvent g), and the solution obtained in this way will be mixed with an aqueous solution of the imidazolinone herbicide in the form of its salt and the other ingredients of the active ingredient concentrate, for example by mixing a solution of the dinitroaniline in constituent g), which comprises at least some of the constituents d), e) and/or f), with an aqueous solution of the salt of the imidazolinone herbicide, which optionally comprises some or all of the constituents d), e) and/or f). In particular, the procedure involves firstly dissolving the dinitroaniline, and also the majority or in particular all of the constituents d), e) and f) in the hydrocarbon solvent, and mixing the solution obtained in this way with an aqueous solution of the salt of the imidazolinone herbicide, which optionally comprises the remainder of constituents d), e) and/or f). The solution of the salt of the imidazolinone herbicide is generally prepared by suspending the free acid of the imidazolinone herbicide in water, followed by a base suitable for salt formation, e.g. an alkali metal hydroxide or carbonate, ammonia or a substituted amine $NR^1R^2R^3$, where optionally excess base is neutralized by adding an acid, e.g. acetic acid. The mixing typically takes place at temperatures from 10° C. to 90° C., in particular from 10° C. to 60° C. Higher temperatures, for example 35° C. or 40° C. or above, are possibly expedient in order to increase the rate of the microemulsion formation. On the other hand, the mixing can as a rule also be carried out at lower temperatures, for example at 10° C. to 35° C.

The invention further provides the use of the active ingredient concentrates described herein for controlling undesired plant growth, in particular for controlling harmful plants in cultivated plants, in particular of harmful plants in cultures of leguminosae, in particular in cultures of leguminous vegetables such as peas and beans. The active ingredient concentrates according to the invention are suitable for controlling a large number of monocotyledonous and dicotyledonous harmful plants, in particular for controlling *polygonum* species, *fumaria* species, *cerastium* species, rhaphanus species, poppy plants, buttercup plants, *anthemis* species, *Aethusa* spp. and *capsella* species.

The active ingredient concentrates according to the invention are typically applied in an amount such that the total amount of the applied active ingredients (total application amount) in the range from 100 to 4500 g/ha, in particular in the range from 200 to 2200 g/ha results. The application amount of imidazolinone herbicide, calculated as free acid, is typically in the range from 5 to 500 g/h, in particular in the range from 10 to 250 g/ha. The application amount of dinitroaniline herbicide is typically in the range from 95 to 4000 g/ha, in particular in the range from 190 to 2000 g/ha.

The application of the active ingredient concentrates according to the invention can take place in the preemergence stage, i.e. before the harmful plants emerge, and also in the postemergence phase. The active ingredient concentrates according to the invention are suitable in particular for controlling harmful plants in the preemergence stage.

The active ingredient concentrates according to the invention are usually applied diluted with water. For this, the active ingredient concentrates according to the invention are diluted with water to the desired application concentration, preferably with at least 50 parts of water, e.g. 50 to 5000 parts of water, in particular with at least 100 parts of water, e.g. 50 to 5000 parts of water, per part by weight of the active ingredient concentrate. The dilution is usually effected by adding the active ingredient concentrate according to the invention to the water. To rapidly mix the concentrate with water, agitation, such as, for example, stirring, is usually used. However, agitation is generally not necessary. Although the temperature is a noncritical factor for the dilution operation, dilutions are usually carried out at temperatures in the range from 0° C. to 50° C., in particular at 10° C. to 30° C. or at ambient temperature. The water used for the dilution is generally tap water. However, the water can already comprise water-soluble compounds which are used in crop protection, such as, for example, nutrients, fertilizers or pesticides.

The following examples serve to illustrate the invention. The following feed materials were used:

Imazamox: purity >95%;
Pendimethalin: purity >95%;
Anionic emulsifier d1): 50-70% by weight solution of calcium dodecylbenzenesulfonate in isobutanol;
Anionic emulsifier d2): 50-70% by weight solution of ammonium dodecylbenzenesulfonate in an aromatic hydrocarbon solvent;
Anionic emulsifier d3): 60-70% by weight solution of sodium dioctylsulfosuccinate in an aromatic hydrocarbon solvent;
Nonionic emulsifier e1): nonionic ethylene oxide-propylene oxide block copolymer, $M_N$ 9000, HLB value 14 (Antarox B500, Rhodia);
Nonionic emulsifier e2): nonionic ethylene oxide-propylene oxide block copolymer, $M_N$ 6000, HLB value 14 (Witconol NS 500K, Akzo Nobel);
Nonionic adjuvant f1): polyoxyethylene (20) sorbitan-monooleate (Polysorbate 20);
Hydrocarbon solvent g): mixture of alkylaromatics with a boiling range of 244-299° C. and a naphthaline content below 0.9% by weight (Solvesso® 200 ND, Exxon);
Concentrated ammonia (34% by weight);
Antifoam 1: polydimethylsiloxane (Rhodorsil 481, Rhodia);
Antifoam 2: aqueous polydimethylsiloxane emulsion (SAG 220, Kurt Obermeier GmbH&Co.KG).

General Preparation Procedure:

Molten pendimethalin was dissolved in the desired amount in the hydrocarbon solvent. To this were added in succession the nonionic adjuvant f1, the anionic emulsifier d1, d2 or d3 and the nonionic emulsifier e1 or e2, and the mixture was stirred until a homogeneous solution was obtained.

Imazamox was suspended in the form of the free acid in the desired amount of water and neutralized with concentrated aqueous ammonia solution, giving a clear solution. The pH of the solution was adjusted to pH 6.4-6.7 using 10% strength acetic acid. The desired amount of disodium hydrogenorthophosphate and potassium dihydrogenorthophosphate was then added and the mixture was stirred until a homogeneous solution of the imazamox-ammonium was obtained.

The solution of the pendimethalin was initially introduced in a high-speed laboratory mixer with rotor-stator arrangement (Silverson L4RT with emulsifying sieve). The antifoam and the aqueous solution of the imazamox-ammonium were added and the mixture was stirred for 10 min at maximum stirring speed.

The composition of Examples 1 to 14 and Comparative examples V1 to V4 is given in Table 1 below:

TABLE 1

| Constituent | V1 | V2 | V3 | V4 |
|---|---|---|---|---|
| Pendimethalin [g/l] | 250 | 250 | 250 | 250 |
| Imazamox | 16.7 | 16.7 | 16.7 | 16.7 |
| Ammonia (34%) [g/l] | 3.9 | 3.9 | 3.9 | 3.9 |
| Water [g/l] | 65 | 65 | 65 | 65 |
| AE d1) [g/l][1) | 32 | 0 | 0 | 0 |
| AE d2) [g/l][1) | 0 | 12.8 | 19.2 | 0 |
| AE d3) [g/l][1) | 0 | 0 | 0 | 15.7 |
| NE e1) [g/l] | 0 | 51.2 | 44.8 | 51.4 |
| NE e2) [g/l] | 32 | 0 | 0 | 0 |
| Adjuvant f1) [g/l] | 167 | 167 | 167 | 167 |
| $KH_2PO_4$ [g/l] | 0.14 | 0.14 | 0.14 | 0.14 |
| $Na_2HPO_4$ [g/l] | 0.05 | 0.05 | 0.05 | 0.05 |
| HS | ad 1 l | ad 1 l | ad 1 l | ad 1 l |

| Constituent | 1 | 2 | 2 | 4 |
|---|---|---|---|---|
| Pendimethalin [g/l] | 250 | 250 | 250 | 250 |
| Imazamox | 16.7 | 16.7 | 16.7 | 16.7 |
| Ammonia (34%) [g/l] | 3.9 | 3.9 | 3.9 | 3.9 |
| Water [g/l] | 65 | 65 | 65 | 65 |
| AE d1) [g/l][1) | 0 | 0 | 0 | 0 |
| AE d2) [g/l][1) | 44.8 | 38.4 | 32 | 25.6 |
| AE d3) [g/l][1) | 0 | 0 | 0 | 0 |
| NE e1) [g/l] | 19.2 | 25.6 | 32 | 38.4 |
| NE e2) [g/l] | 0 | 0 | 0 | 0 |
| Adjuvant f1) [g/l] | 167 | 167 | 167 | 167 |
| $KH_2PO_4$ [g/l] | 0.14 | 0.14 | 0.14 | 0.14 |
| $Na_2HPO_4$ [g/l] | 0.05 | 0.05 | 0.05 | 0.05 |
| HS | ad 1 l | Ad 1 l | ad 1 l | ad 1 l |

| Constituent | 5 | 6 | 7 | 8 | 9 |
|---|---|---|---|---|---|
| Pendimethalin [g/l] | 250 | 250 | 250 | 250 | 250 |
| Imazamox | 16.7 | 16.7 | 16.7 | 16.7 | 16.7 |
| Ammonia (34%) [g/l] | 3.9 | 3.9 | 3.9 | 3.9 | 3.9 |
| Water [g/l] | 65 | 65 | 65 | 65 | 65 |
| AE d1) [g/l][1) | 0 | 0 | 0 | 0 | 0 |
| AE d2) [g/l][1) | 0 | 0 | 0 | 0 | 0 |
| AE d3) [g/l][1) | 62.8 | 54.9 | 47.1 | 39.2 | 31.3 |
| NE e1) [g/l] | 12.9 | 17.2 | 25.7 | 32.1 | 38.5 |
| NE e2) [g/l] | 0 | 0 | 0 | 0 | 0 |
| Adjuvant f1) [g/l] | 167 | 167 | 167 | 167 | 167 |
| $KH_2PO_4$ [g/l] | 0.14 | 0.14 | 0.14 | 0.14 | 0.14 |
| $Na_2HPO_4$ [g/l] | 0.05 | 0.05 | 0.05 | 0.05 | 0.05 |
| HS | ad 1 l | ad 1 l | ad 1 l | ad 1 l | ad 1 l |

| Constituent | 10 | 11 | 12 | 13 | 14 |
|---|---|---|---|---|---|
| Pendimethalin [g/l] | 250 | 250 | 250 | 250 | 250 |
| Imazamox | 16.7 | 16.7 | 16.7 | 16.7 | 16.7 |
| Ammonia (34%) [g/l] | 3.9 | 3.9 | 3.9 | 3.9 | 3.9 |
| Water [g/l] | 65 | 65 | 65 | 65 | 65 |
| AE d1) [g/l][1) | 0 | 0 | 0 | 0 | 0 |
| AE d2) [g/l][1) | 28.8 | 25.6 | 0 | 0 | 0 |
| AE d3) [g/l][1) | 0 | 0 | 53.8 | 50 | 46 |
| NE e1) [g/l] | 35.2 | 38.4 | 19.3 | 22.5 | 25.5 |
| NE e2) [g/l] | 0 | 0 | 0 | 0 | 0 |
| Adjuvant f1) [g/l] | 167 | 167 | 167 | 167 | 167 |
| $KH_2PO_4$ [g/l] | 0.14 | 0.14 | 0.14 | 0.14 | 0.14 |
| $Na_2HPO_4$ [g/l] | 0.05 | 0.05 | 0.05 | 0.05 | 0.05 |
| HS | ad 1 l | ad 1 l | ad 1 l | ad 1 l | ad 1 l |

AE = Anionic emulsifier,
NE = Nonionic emulsifier,
HS = Hydrocarbon solvent
[1)]The amount of emulsifier solution actually used is stated Testing the Formulations:

To determine the chemical stability of the formulation, the content of pendimethalin was determined by methods known in the literature as was the content of imazamox by means of reversed phase HPLC (chromatography column e.g. Zorbax Eclipse model 250×4.6 mm; eluent e.g. acetonitrile/water/tetrahydrofuran mixture) before and after storage.

To determine the physical stability, the formulations in each case were stored in cuvettes at the desired temperature over a certain period and then the cloudiness and/or the formation of a phase separation was assessed.

To determine the dilution stability, the formulations were added at 30° C. with stirring to CIPAC-A water or CIPAC D water such that a certain concentration of the formulation resulted. The dilutions were then stored in a measuring cylinder for up to 24 h and the formation of foam, oil or cream was assessed.

COMPARATIVE EXAMPLE 1

The active ingredient concentrate from Comparative example 1 exhibited no phase separation after 4 weeks at −5° C. After 12 weeks at 40° C. and after 2 weeks at 54° C., a sparingly soluble precipitate had formed.

Upon dilution of the active ingredient concentrate from Comparative example 1 with CIPAC-A water or CIPAC-D water to concentrations of 4.5% v/v and to 1.1% v/v, emulsions were spontaneously obtained which, even after 24 h at 20° C., exhibited no phase separation.

EXAMPLES 1 to 4 COMPARATIVE EXAMPLES V2 and V3

The active ingredient concentrates of Examples 1 to 4 and of Comparative examples V2 and V3 were stored for 10 days at 20° C. and assessed with regard to the optical appearance. The active ingredient concentrates of Examples 1 to 4 directly after preparation were slightly cloudy, whereas in the case of the active ingredient concentrates of the Comparative examples V2 and V3, a significant separation into 2 or more phases was observed. After 10 days at 20° C., the active ingredient concentrates of Examples 1 and 4 were slightly cloudy and the active ingredient concentrates of Examples 2 and 3 were clear. The active ingredient concentrates of Comparative examples V2 and V3 were cloudy opaque after shaking and, in the case of Comparative example V3, clearly exhibited 2 phases.

To determine the thermal stability, samples of the active ingredient concentrates of Examples 1 to 4 and of Comparative example V3 were stored in cuvettes in each case for one hour at 25, 30, 40, 45, 50 and 54° C., and then the optical appearance was assessed visually. The results are summarized in Table 2:

TABLE 2

| Storage temperature [° C.] | 1 | 2 | 3 | 4 | V3 |
|---|---|---|---|---|---|
| 54 | cloudy | cloudy | cloudy | clear | phase separation |
| 50 | cloudy | cloudy | cloudy | clear | phase separation |
| 45 | cloudy | cloudy | clear | clear | phase separation |
| 40 | cloudy | cloudy | clear | clear | phase separation |
| 30 | cloudy | clear | clear | clear | phase separation |
| 25 | clear | clear | clear | clear | phase separation |

To determine the dilution stability, the active ingredient concentrates were diluted with CIPAC-A water or CIPAC-D water in each case to concentrations of 4.5% v/v and also to 0.33% v/v. With the exception of Comparative example V2, emulsions were spontaneously obtained in all cases. In each case 100 ml of the resulting emulsions were stored for 2 h at 30° C. in a measuring cylinder and then the formation of oil or cream was determined. The results are summarized in Table 3 below:

TABLE 3

| | 1 | 2 | 3 | 4 | V2 |
|---|---|---|---|---|---|
| Dilution with CIPAC-A water to 4.5% v/v | | | | | |
| Oil [ml] | 0 | 0 | 0 | 0 | 2 |
| Cream [ml] | 0 | 0 | 0 | 0 | |

TABLE 3-continued

| | 1 | 2 | 3 | 4 | V2 |
|---|---|---|---|---|---|
| Dilution with CIPAC-D water to 4.5% v/v | | | | | |
| Oil [ml] | 0 | 0 | 0 | 0 | 2 |
| Cream [ml] | 0 | 0 | 0 | 0 | |
| Dilution with CIPAC-A water to 0.33% v/v | | | | | |
| Oil [ml] | 0 | 0 | 0 | 0 | 0 |
| Cream [ml] | 0 | 0 | 0 | 0 | 0.5 |
| Dilution with CIPAC-D water to 0.33% v/v | | | | | |
| Oil [ml] | 0 | 0 | 0 | 0 | 0 |
| Cream [ml] | 0 | 0 | 0 | 0 | 0.5 |

EXAMPLES 5 to 9 COMPARATIVE EXAMPLE V4

To determine the thermal stability, samples of the active ingredient concentrates of Examples 5 to 9 and of Comparative example V4 were stored in cuvettes in each case for one hour at −5, 0, 54, 60, 65, 70, 75 and 80° C. and also −10 to +10° C. (temperature cycle, in each case 12 h oscillating, 5 cycles) and then the optical appearance was assessed visually. The results are summarized in Table 4:

TABLE 4

| Storage temperature [° C.] | 5 | 6 | 7 | 8 | 9 | V4 |
|---|---|---|---|---|---|---|
| 80 | ++ | ++ | ++ | − | − | − |
| 75 | ++ | ++ | ++ | ++ | − | − |
| 70 | ++ | ++ | ++ | ++ | − | − |
| 65 | ++ | ++ | ++ | ++ | o | − |
| 60 | ++ | ++ | ++ | ++ | + | − |
| 54 | ++ | ++ | ++ | ++ | ++ | − |
| 0 | ++ | ++ | ++ | + | + | − |
| −5 | ++ | ++ | ++ | + | + | − |
| −10/+10 | ++ | ++ | ++ | + | + | − |

"++" = clear, "+" = slightly cloudy, "o" = cloudy, "−" phase separation

EXAMPLES 10 to 14

To determine the thermal stability, samples of the active ingredient concentrates of Examples 10 to 14 were stored in cuvettes in each case for 8 weeks at −10, −5, 0, 10, 23, 30, 40 and 50° C. and also at −10 to +10° C. (temperature cycle, in each case 12 h oscillating, 5 cycles) and then the optical appearance was assessed visually. The results are summarized in Table 5:

TABLE 5

| Storage temperature [° C.] | 10 | 11 | 12 | 13 | 14 |
|---|---|---|---|---|---|
| 50 | + | + | + | + | + |
| 40 | + | + | + | + | + |
| 30 | + | + | + | + | + |
| 23 | + | + | + | + | + |
| 10 | + | + | + | + | + |
| 0 | o | − | + | + | + |
| −5 | + | − | + | + | + |
| −10 | − | − | + | + | + |
| −10/+10 | ++ | ++ | + | + | + |

"++" = clear, "+" = slightly cloudy, "o" = cloudy, "−" phase separation

To determine the dilution stability, the active ingredient concentrate from Example 13 was diluted with CIPAC-A water or CIPAC-D water directly after its preparation and also following storage for 2 weeks at 54° C. in each case to concentrations of 4.5% v/v and to 0.5% v/v. The emulsion formation took place in all cases without problems. The resulting emulsions were assessed with regard to the formation of oil or cream in each case 30 min, 2 h and 24 h following dilution and storage of the emulsion at 30° C. With the exception of the active ingredient concentrates diluted to 4.5% v/v, at no point was the formation of oil, cream or sediment observed in the resulting emulsions. The emulsions which had been prepared by diluting the freshly prepared active ingredient concentrate with CIPAC-A or with CIPAC-D water to 4.5% v/v exhibited no formation of oil, cream or sediment at 30 min and 2 h. After 24 h, traces of sediment were observed which could be reemulsified without problems by shaking the emulsion. The emulsions which had been prepared by diluting the active ingredient concentrate stored for 2 weeks at 54° C. with CIPAC-A or with CIPAC-D water to 4.5% v/v exhibited no formation of oil, cream or sediment at 30 min and 2 h. After 24 h, traces of sediment were observed which could be reemulsified without problems by shaking the emulsion.

The invention claimed is:

1. A liquid, water-emulsifiable active ingredient concentrate comprising the following constituents:
    a) 100 to 400 g/l of at least one herbicidal dinitroaniline, where the herbicidal dinitroaniline is pendimethalin;
    b) 5 to 100 g/l of at least one imidazolinone herbicide, where the herbicidal imidazolinone herbicide is imazamox, in the form of its ammonium salt or substituted ammonium salt;
    c) 20 to 100 g/l of water;
    d) 15 to 150 g/l of at least one anionic surface-active substance which is selected from sodium and ammonium salts of $C_4$-$C_{20}$-alkylbenzenesulfonic acids, of $C_8$-$C_{22}$-alkylsulfuric acid half-esters and of mono- and di-$C_4$-$C_{18}$-alkyl esters of sulfosuccinic acid and mixtures thereof;
    e) 5 to 100 g/l of at least one polymeric, nonionic surface-active substance which is selected from ethylene oxide-co-propylene oxide block copolymers;
    f) 100 to 250 g/l of at least one nonionic surface-active substance selected from ethoxylated fatty acid esters of polyhydroxyl compounds, alkyl polyglucosides, ethoxylated $C_4$-$C_{16}$-alkylphenols and ethoxylated $C_8$-$C_{22}$-alkanols; and
    g) at least one hydrocarbon solvent up to 1 L;
    where the quantitative data of components a) to f) in g/l are based on the total volume of the active ingredient concentrate.

2. The active ingredient concentrate according to claim 1, where the weight ratio of constituent a) to constituent b) is in the range from 2:1 to 50:1.

3. The active ingredient concentrate according to claim 1, where component d) is selected from the ammonium salts of $C_4$-$C_{20}$-alkylbenzenesulfonic acids.

4. The active ingredient concentrate according to claim 1, where constituent e) has a number-average molecular weight in the range from 1500 to 100000 Daltons.

5. The active ingredient concentrate according to claim 1, where the weight ratio of constituent d) to constituent e) is in the range from 20:1 to 1:5.

6. The active ingredient concentrate according to claim 1, in which constituent f) is selected from ethoxylated sorbitan fatty acid esters.

7. The active ingredient concentrate according to claim 1, where constituent g) is selected from alkylaromatics.

8. The active ingredient concentrate according to claim 1, comprising less than 200 ppm of polyvalent metal cations.

9. The active ingredient concentrate according to claim 1, additionally comprising at least one inorganic buffer.

10. The active ingredient concentrate according to claim 1, where constituents a) to g) constitute at least 99% by weight of the active ingredient concentrate.

11. A method of controlling undesired plant growth comprising treating the plant or a locus where the plant may grow, prior to or after emergence, with the concentrate of claim 1 and an additive or a diluent.

12. The method of claim 11, where the herbicidal dinitroaniline is pendimethalin.

13. The method of claim 11, where the herbicidal imidazolinone herbicide is imazamox.

14. The method of claim 11, where the weight ratio of constituent a) to constituent b) is in the range from 2:1 to 50:1.

15. The method of claim 11, where component d) is selected from sodium and ammonium salts of $C_4$-$C_{20}$-alkylbenzenesulfonic acids, of $C_8$-$C_{22}$-alkylsulfuric acid half-esters and of mono- and di-$C_4$-$C_{18}$-alkyl esters of sulfosuccinic acid and mixtures thereof.

16. The method of claim 15, where component d) is selected from the ammonium salts of $C_4$-$C_{20}$-alkylbenzenesulfonic acids.

* * * * *